(12) United States Patent
Ghai et al.

(10) Patent No.: US 6,790,869 B2
(45) Date of Patent: Sep. 14, 2004

(54) RESVERATROL ANALOGS FOR PREVENTION OF DISEASE

(75) Inventors: Geetha Ghai, Murray Hill, NJ (US); Kuang Yu Chen, Belle Mead, NJ (US); Robert T. Rosen, Monroe Township, NJ (US); Mingfu Wang, Piscataway, NJ (US); Nitin Telang, Pelham Manor, NY (US); Martin Lipkin, New York, NY (US); Chi-Tang H, East Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 74 days.

(21) Appl. No.: 09/860,919

(22) Filed: May 18, 2001

(65) Prior Publication Data

US 2002/0028852 A1 Mar. 7, 2002

Related U.S. Application Data

(63) Continuation of application No. PCT/US00/25799, filed on Sep. 20, 2000.
(60) Provisional application No. 60/155,019, filed on Sep. 21, 1999.

(51) Int. Cl.$^7$ ............................................. A61K 31/045
(52) U.S. Cl. ........................................ 514/738; 514/724
(58) Field of Search ........................................ 514/938

(56) References Cited

U.S. PATENT DOCUMENTS

| | | | | |
|---|---|---|---|---|
| 5,314,693 A | * | 5/1994 | Suga | 424/196 |
| 5,430,062 A | * | 7/1995 | Cushman et al. | 514/646 |
| 5,747,536 A | | 5/1998 | Cavazza | 514/556 |
| 6,147,121 A | * | 11/2000 | Breton et al. | 514/726 |
| 6,407,142 B1 | * | 6/2002 | Courbriere et al. | 514/736 |

FOREIGN PATENT DOCUMENTS

| | | |
|---|---|---|
| JP | 61-171427 | 8/1986 |
| JP | 9-328410 | 12/1997 |
| WO | WO 99/03816 | 1/1999 |
| WO | WO 99/04747 | 4/1999 |

OTHER PUBLICATIONS

Ali et al. "Studies on crude drugs effective on visceral larva migrans, XV. Synthesis and nematocidal activity of hydroxystilbenes" Chemical & Pharmceutical Bulletin, 1992, 40(5), pp. 1130–1136.*

Wang et al. "Evaluation of Resveratrol Derivatives as Potential Antioxidants and Identification of a Reaction Product of Resveratrol and 2,2–Diphenyl–1–picryhydrazyl Radical" Journal of Agricultural and Food Chemistry, Sep. 14, 1999, 47 (10), pp. 3974–3977.*

Thakkar et al. "Synthesis and protein–tyrosine kinase inhibitory activity of polyhydroxylated stilbene analgs of piceattanol" Journal of Medicinal Chemistry (1993), 36 (20), pp. 2950–2955.*

Castro et al. "Isoflavans and a stilbene from wood of the decay–resistant tropical tree *Diphsa robinioides*" Journal of Natural Products (1986), 49(4), pp. 680–683.*

Cushman et al., "Synthesis and evaluation of analogs of (Z)–1–(4–methoxyyphenyl)–2–(3,4,5–trimethoxyphenyl)ethene as potential cytotoxic and antimitotic agents", *J. Med. Chem.* 1992 35(12):2293–2306.

Breton et al., "Use of hydroxystilbenes in a skin–fortifying composition", *Caplus on ACS* 2000 3327.

* cited by examiner

*Primary Examiner*—Sreeni Padmanabhan
*Assistant Examiner*—Jennifer Kim
(74) *Attorney, Agent, or Firm*—Reed Smith LLP; William J. McNichol, Jr.; Nanda P.B.A. Kumar

(57) ABSTRACT

Compositions and methods for prevention or treatment of disease are provided which comprise analogs of Resveratrol.

1 Claim, No Drawings

RESVERATROL ANALOGS FOR PREVENTION OF DISEASE

INTRODUCTION

This application is a continuation of PCT Application No. PCT/US00/25799 filed Sep. 20, 2000, which claims the benefit of U.S. Provisional Patent Application No. 60/155,019 filed Sep. 21, 1999.

BACKGROUND OF THE INVENTION

Naturally occurring non-nutritive agents such as flavonoids, phenolic compounds, glucosinulates, terpenes and many others present in plants are believed to have disease preventive properties. Diets containing some of these substances have been shown to be protective against diseases such as colon and breast cancer in animals (Kuo, S. M. 1997. *Clin. Rev. Oncogenesis* 8:47–69; Verhoeven et al. 1996. *Cancer Epid. Biomark. Prev.* 5:733–748; Bradlow et al. 1991. *Carcinogenesis* 12:1571–1574; Lamartiniere et al. 1995. *Proc. Soc. Exp. Biol. Med.* 208:120–123). The clinical relevance of such natural phytochemicals is dependent on extrapolation from epidemiological data and from experiments in animal models of diseases of interest.

Resveratrol (3,5,4'-trihydroxystilbene) and its glucoside, cis- and trans-forms occur naturally in foods such as grapes, mulberries, peanuts, and wine. Resveratrol and its related compounds also are found in other plants including a traditional Chinese medicinal plant, the dried roots of *Polygonum cuspidatum*. These polyphenolic compounds possess many biological activities including antioxidant activity, antimutagenic activity, antiinflammatory activity, anti-tumor promoting activity, as well as demonstrating a preventive effect for cancer (Jang et al. 1997. *Science* 275:218–220). Resveratrol has also been shown to affect a variety of specific cellular mediators. For example, studies have shown that resveratrol induces nitric oxide synthase (Hsieh et al. 1999. *Cancer Res.* 59:2596–2601), that resveratrol inhibits 12-O-tetradecanoylphorbol-13-acetate-induced cyclooxygenase-2 gene expression (Subbaramiah wt al. 1998. *J. Biol. Chem.* 273:21875–21882), that resveratrol inhibits expression of tissue factor and cytokines in vascular cells (Pendurthi et al. 1999. *Arterioscler. Thromb. Vasc. Biol.* 19:419–426), and that resveratrol inhibits ribonucleotide reductase and DNA synthesis in mammalian cells (Fontecave et al. 1998. *FEBS Lett.* 421:277–279).

Much attention has been focused on the fact that large amounts of resveratrol are present in red wine and that moderate red wine consumption may reduce the risk of cardiovascular disease (Goldberg et al. 1995. *Clin. Chim. Acta* 237:155–187). In addition, evidence has accumulated to support a role for resveratrol in prevention of cancer and heart disease (Constant, J. 1997. *Coron. Artery Dis.* 8:645–649; Fontecave et al. 1998. *FEBS Lett.* 421:277–279).

WO 9904747 describes the use of resveratrol to improve the appearance of human skin and to enhance differentiation and inhibit proliferation of keratinocytes. Resveratrol in pure form is given as a topical formulation in doses of 0.00002 to 10% resveratrol by weight.

WO 9903816 discloses compositions of resveratrol esters and their oligomers for use as anti-tumor and vasoprotective agents in animals and humans. The resveratrol derivatives are monomer or oliogomers having at least one ester group with the formula —O—CO—A. None of the compounds are resveratrol analogs with hydroxyl or methoxy substitutions on the rings.

WO 9901148 describes compositions containing resveratrol and other polyphenols for the treatment of metabolic disorders such as anoxia. The polyphenols are extracts from grapes and grape products or wine with yeast extracts combined.

A Japanese patent (JP 9328410) discusses the use of an extract of the Yucca plant which contains saponin, flavone and resveratrol as a cosmetic for prevention of rough skin and cutaneous aging. The extract was shown to have antimicrobial activity as well as UV absorbing ability.

CN 1127070 describes use of resveratrol in combination with a variety of other compounds as additives for a nutritional milk powder. The powder was developed for use in the elderly for immunostimulation and prevention of heart disease, as well as a milk powder for pregnant women and children and a health drink for athletes.

U.S. Pat. No. 5,747,536 discloses use of a trihydroxy or tetrahydroxystilbene, such as resveratrol, in combination with L-carnitine and alkanoyl L-carnitine to prevent or treat cardiovascular diseases, peripheral cardiopathies, and diabetic peripheral neuropathies.

Another Japanese patent (JP 61171427) describes use of an extract of Polygonaceae as an anti-thrombosis agent. The extract contains a stilbene compound comprising resveratrol as well as other components.

It has now been found that analogs of the natural product resveratrol with additional hydroxy or methoxy substitutions have biological activity that can lead to disease prevention.

SUMMARY OF THE INVENTION

An object of the present invention is composition comprising an analog of resveratrol, preferably a hydroxylated or methoxylated resveratrol including 3,5-dihydroxystilbene (R-1), 3,3',4,5'-tetrahydroxystilbene (R-2), 3,4,4',5-tetrahydroxystilbene (R-3), 3,3',5,5'-tetrahydroxystilbene (R-4), 3,3',4,5,5'-pentahydroxystilbene (R-5), 3,5-dimethoxystilbene (MR-1), 3,4',5-trimethoxystilbene (MR-0), 3,3',4,5'-tetramethoxystilbene (MR-2), 3,4,4',5-tetramethoxystilbene (MR-3), 3,3',5'5'-tetramethoxystilbene (MR-4), and 3,3',4,5,5'-pentamethoxystilbene (MR-5).

Another object of the present invention is a method for inhibiting cell growth comprising administering the composition.

Yet another object of the present invention is a method for preventing or treating cancer in an animal which comprises administration of the composition.

DETAILED DESCRIPTION OF THE INVENTION

Although there are reports of the biological activity and efficacy of resveratrol as a disease preventive agent, analogs of this compound have not been examined or described as disease preventive agents. In the context of the present invention "analog" is a compound that is comprised of resveratrol with substituted groups attached to the parent compound to produce a chemically-modified resveratrol compound. Five hydroxy and six methoxy analogs of resveratrol were synthesized using standard chemical methodology. Each analog is a novel analog that was then tested for biological activity. The analogs produced and tested included 3,5-dihydroxystilbene (R-1), 3,3',4,5'-tetrahydroxystilbene (R-2), 3,4,4',5-tetrahydroxystilbene (R-3), 3,3',5,5'-tetrahydroxystilbene (R-4), 3,3',4,5,5'-pentahydroxystilbene (R-5), 3,5-dimethoxystilbene (MR-1), 3,4',5-trimethoxystilbene (MR-0), 3,3',4,5'- tetramethoxystilbene (MR-2), 3,4,4',5-tetramethoxystilbene (MR-3), 3,3',5'5'-tetramethoxystilbene (MR-4), and 3,3',4,5,5'-pentamethoxystilbene (MR-5). The activity of the analogs was compared with that of the parent compound resveratrol (3,4',5-trihydroxystilbene) in several in vitro and in vivo models.

Initial tests examined the potential cancer preventive activity of the analogs. Resveratrol and its analogs were evaluated in W138 and SV40 transformed W138VA cells and in preneoplastic 184-B5/HER and neoplastic SK-BR-3 human mammary epithelial cells. Cell proliferation, apoptosis, and gene expression studies were conducted using standard methodologies.

W138 human diploid fibroblasts and cancerous SV40-transformed W138 cells (W138VA) were used in a cell proliferation assay. Growth rate and viability of these cells was determined following addition of each analog. Doses tested ranged from 50 ng to 300 μg per ml or 1 μM to 100 μM concentrations in culture media. Cell cultures were grown for 5 days in the presence of the various doses of analogs. Growth rate was measured by counting viable cells using the trypan blue dye exclusion method. Results are presented below in Table 1. Resveratrol inhibited cell growth at low concentrations, less than 10 μM. When the analogs were tested, R-3 also inhibited cell growth but was 10-fold less effective than resveratrol. Methylation of resveratrol to form MR-0 did not significantly affect the ability of resveratrol to inhibit cell growth in W138VA cells, although MR-0 was less effective than resveratrol in W138 cells. Not all of the methylated analogs exhibited this differential growth inhibitory effect. Of the methylated analogs, MR-3 was most effective in inhibiting cell growth. At a concentration of 1 μM, MR-3 completely blocked proliferation of W138VA cells, although it had no effect on growth of W138 cells. MR-1 was not active as an inhibitor of cell growth even at doses as high as 100 μM. MR-4 inhibited growth of W138 cells but not W138VA cells at doses of 100 μM. These data demonstrate that there are structure-activity differences between the analogs in terms of inhibition of cell proliferation.

TABLE 1

Growth Rate in Cells Following Exposure to Resveratrol Analogs

| Analog Tested | Cell Line | |
| --- | --- | --- |
| | W138 Cells | W138VA Cells |
| R0 (10 μM)[1] | +[2] | + |
| R1 | ND[3] | ND |
| R2 | ND | ND |
| R3 (10 μM) | + | + |
| R4 | ND | ND |
| R5 | ND | ND |
| MR0 (100 μM) | + | + |
| MR1 (100 μM) | —[4] | — |
| MR2 | ND | ND |
| MR3 (1 μM) | — | + |
| MR4 (100 μM) | + | — |
| MR5 (100 μM) | + | + |

[1]Value in parentheses is the effective concentration for growth inhibition.
[2]+ = >60% growth inhibition.
[3]ND = not determined
[4]— = no effect or only slight inhibition observed In addition to inhibition of cell growth, treatment of W138 and W138VA cells with analogs led to morphological changes in the cells. Treatment of W138 cells with resveratrol and its analogs R-1 and R-3 led to elongation of normal W138 cells. Methoxy analogs such as MR-0 and MR-3 caused the flattening of W138 cells. The flattening of the cells was accompanied by an increase in neutral β-galactosidase activity as indicated by an increase in staining. An increase in activity of β-galactosidase is characteristic of senescent cells, indicating that these analogs modulate the life-span of normal cells.

Resveratrol and its analogs were also tested in 184-B5/HER cells. Results showed that there was a dose-dependent inhibition of growth in response to treatment with resveratrol as well as the methoxy derivatives MR-0, MR-2 and MR-3. The concentration that inhibited growth by 50% ($IC_{50}$) for the tested compounds were: Resveratrol, 10.5 μM; MR-0, 10.5 μM; MR-2 120 μM; MR-3, 1.0 μM. A cell cycle analysis revealed that treatment with MR-0, MR-2 and MR-3 resulted in progressive arrest of cell in the G2/M phase relative to solvent-treated control cultures and that MR-3 was the most effective compound.

The effect of the analogs on apoptosis was also examined. Apoptosis is characterized by nuclear DNA fragmentation that is mediated through a variety of signal transduction pathways. An assay was used that relies on fluorescent labeling of fragmented DNA. Results showed that R-3 induced apoptosis in W138VA cells, but not in W138 cells. In 184-B5/HER cells, resveratrol, MR-0 and MR-2 induced apoptosis to a significantly greater extent than solvent-treated control cells, while MR-3 had no effect on apoptosis.

Cell colony formation was also examined in 184-B5/HER cells. Consistent with the effect on cell cycle progression and apoptosis, resveratrol, MR-0, MR-2 and MR-3 exhibited differential inhibition of colony formation in response to continuous treatment with a 4 μM dose of each analog. Resveratrol, MR-0 and MR-2 produced approximately 25–40% inhibition in the anchorage-dependent colony formation assay. MR-3, however, produced almost a 80% inhibition of colony formation.

Targeted gene assay was then performed using RT-PCR. Both normal (W138) and cancerous (W138VA) cells at resting phase (G0) were treated with 10–15% fetal bovine serum to initiate growth stimulation. Cells were then harvested at various time points during cell cycle progression. Total RNA was prepared from these cells according to standard RT-PCR methods. Paired gene specific primers were prepared and used including human glyceraldehyde-3-phosphate dehydrogenase HG3PDH), c-fos, c-myc, ornithine decarboxylase (ODC), proliferating cell nuclear antigen (PCNA), thymidine kinase (TK), cyclooxygenase 2 (COX2), BRCA1, BRCA2, p53, APC, MCC, pRb, cyclooxygenase 1 (COX1), bc12, and Bax. Results showed that expression of HG3PDH, a housekeeping gene, remained constant throughout the progression of the cell cycle in the control cells. Treatment with resveratrol or MR-3 did not affect the expression. Expression of c-fos and c-myc, an early G1 event in normal W138 cells, were both deregulated in transformed W138VA cells. Treatment with resveratrol and MR-3 did not significantly affect the expression of these two genes. Similarly, treatment of cells, both normal and transformed, with either resveratrol or MR-3 had no effect on expression of ODC, PCNA, or TK genes (all cell cycle dependent genes). MR-3 stimulated the expression of COX2 in W138VA cells but not in W138 cells.

Both resveratrol and MR-3 completely abolished expression of BRCA1 and BRCA2 genes in human cells at all time points examined. At equal doses, MR-3 was more potent than resveratrol in inhibiting expression of BRCA genes. Both BRCA1 and BRCA2 are breast cancer genes that together appear to be responsible for more than 60% of total hereditary breast cancers. Therefore, resveratrol and its analogs appear to modulate the breast cancer genes.

The in vivo tumor inhibitory effects of MR-3 were tested in an orthotransplant model. Mice were transplanted with an oncogene expression preneoplastic breast epithelial cells. Mice were then divided into groups with the control group fed AIN-76A diet alone. Another group of mice was fed AIN-76A diet supplemented with 400 ppm MR-3. After 12 weeks of continuous feeding, all mice in the control group exhibited palpable tumor formation at the transplant sites (100% tumor incidence). In contrast, the group fed diet supplemented with the analog MR-3 had a 20% tumor incidence, with only one mouse of the five tested exhibiting tumor growth. Weight gains in the groups were comparable indicating that the analog had little toxicity.

These studies both in vitro and in vivo indicate that analogs of resveratrol have biological activity related to preventing progression of cancer in cells.

In the present invention, analogs of resveratrol can be synthesized in the laboratory or prepared as extracts from plant material, as many resveratrol analogs are known in nature. Animal diets and human or animal dietary supplements can be prepared using the chemically synthesized analog or the plant extract material. One of skill would be able to extract plants material and isolate analogs based on the structures provided in the instant invention for active resveratrol analogs.

To examine the activity of resveratrol-related plant extracts, roots of *Polygonum cuspidatum* were extracted and purified. The final extract prepared was 30% resveratrol which contained 16% trans- and 22% cis- resveratrol, 45% piceid, and 40% stilbenes that contained 22% trans-piceid, 2% cis-piceid, 8% trans-resveratrol, and 8% cis-resveratrol. The inhibitory effect of these three fractions on DNA and RNA synthesis in HL-60 cells and the metabolism of DBMA by mouse liver microsomes was then examined.

All three fractions inhibited DNA and RNA synthesis in a dose-dependent manner. Increasing doses of each fraction reduced the uptake of radioactive thymidine and uridine into DNA and RNA of HL-60 cells. The three fractions had similar potency. All three fractions also inhibited DBMA metabolism by mouse liver microsomes in a dose-dependent manner, with similar potency. These results provide evidence that natural plant extracts can be tested for potential biological activity as compared to resveratrol. Purified resveratrol analogs extracted from plants could be tested in similar experiments.

These data on resveratrol and its hydroxylated and methoxylated analogs support the development of foods and dietary supplements which comprise resveratrol or its analogs for animal consumption. For purposes of the present invention by "animal" it is meant to include humans. These foods and supplements are referred to by those of skill in the art as "nutraceuticals". Compositions of the instant invention would be useful as nutraceuticals for prevention or treatment of diseases associated with cellular proliferation that would include but not be limited to cancer. In a preferred embodiment, the analogs would be used to prevent or treat colon, breast or prostate cancer. One of skill would be able to use the results of experiments in cells and animals to determine effective amounts to be administered to other animals, including humans. By "effective amount" it is meant a concentration that inhibits cellular proliferation either in vitro in cells or in vivo in animals. For example, human test doses can be extrapolated from effective doses in cell studies, such as $IC_{50}$ values, or from effective doses in vivo by extrapolating on a body weight or surface area basis. Such extrapolations are routine in the art.

Compositions comprising resveratrol and its analogs can be formulated for administration as a food supplement using one or more fillers. Alternatively, compositions comprising these extracts can be administered as conventional pharmaceuticals using one or more physiologically acceptable carriers or excipients. Nutraceutical compositions can be formulated for administration by any route including, but not limited to, inhalation or insufflation (through mouth or nose), oral, buccal, parenteral, vaginal, or rectal administration. In one embodiment, oral administration, the compositions are added directly to foods and ingested as part of a normal meal. Various methods are known to those skilled in the art for addition or incorporation of nutraceuticals into foods.

Compositions for use in the present invention can also be administered in the form or tablets or capsules prepared by conventional means with pharmaceutically acceptable excipients such as binding agents, fillers, lubricants, disintegrants, or wetting agents. Examples of specific compounds for use in formulating tablets and capsules are described in detail in the U.S. Pharmacopeia. Tablets comprising the extract can also be coated by methods well known in the art. Liquid preparations for oral administration can also be used. Liquid preparations can be in the form of solutions, syrups or suspensions, or a dry product for reconstitution with water or another suitable vehicle before use. Such liquid preparations can be prepared by conventional means with pharmaceutically acceptable additives such as suspending agents, emulsifying agents, non-aqueous vehicles, and preservatives. Again, specific additives are well known to those of skill and are listed in places such as the U.S. Pharmacopeia. In one embodiment, the oral preparation is formulated to provide controlled time release of the active nutraceutical components. For buccal administration the extract can be formulated as a tablet or lozenge.

For administration by inhalation, compositions for use in the present invention can be delivered in the form of an aerosol spray in a pressurized package or as a nebulizer, with use of suitable propellants. In the case of a pressurized aerosol, the dosage unit can be determined by providing a valve to deliver a metered dose.

Parenterally administered compositions are formulated to allow for injection, either as a bolus or as a continuous infusion. Formulations for injection can be prepared in unit dosage forms, such as ampules, or in multi-dose units, with added preservatives. The compositions for injection can be in the form of suspensions, solutions, or emulsions, in either oily or aqueous vehicles. They may also contain formulatory agents such as suspending agents, stabilizing agents, and/or dispersing agents. The active ingredient may also be presented in powder form for reconstitution with a suitable vehicle before use. Specific examples of formulating agents for parenteral injection are found in the U.S. Pharmacopeia.

For rectal administration or vaginal administration, compositions for use in of the present invention can be formulated as suppositories, creams, gels, or retention enemas.

For dietary supplements, the extract can be added in concentrations up to 5% by weight and mixed according to methods routine in the art. Dietary supplements for animals can be prepared in a variety of forms including, but not limited to, liquid, powder, or solid pill forms.

The efficacy of resveratrol analogs appears to be enhanced by increasing hydrophobicity of the parent resveratrol molecule with hydroxylation and/or methoxylation. One of skill would choose appropriate analogs for testing based on the results presented above for hydroxylated and methoxylated analogs. For example, the analogs would be tested first in vitro for activity in cells and then in vivo for whole animal activity. The analogs with pharmacological activity both in vitro and in vivo would then be tested for therapeutic activity. Analogs would be administered to animals either alone or in combination, where combining analogs would lead to synergistic effects of the resveratrol-related analogs. The combined therapy is supported by results showing that analogs have effects on different stages of the cell cycle and on expression of different gene products.

In the present invention, resveratrol and its analogs can administered either alone or in combination with other compounds/phytochemicals known to affect cellular proliferation and tumor cell growth, where combining compounds would lead to synergistic effects. Compounds or extracts that could be used in combination with resveratrol analogs would include resveratrol itself, which has been shown in the experiments discussed above to be effective in inhibiting tumor cell growth. Many plants, such as Mexican Bamboo and Huzhang, contain high amounts of resveratrol. Resveratrol is a well-known biologically active phytochemical, as shown in experiments where activity of resveratrol was tested as well as the analogs. In addition to resveratrol, other compounds or extracts which could be used in combination with resveratrol analogs would include but not be limited to rosemary extract, black tea extracts, Mexican Bamboo extracts, and Huzhang extracts.

Extracts of rosemary have been shown to have anti-tumor activity and chemopreventive properties (Huang et al. 1994. *Cancer Res.* 54:701–708; Tokuda et al. 1986. *Cancer Lett.* 33:279–285; Singletary et al. 1996. *Cancer Lett.* 104:43–48; Singletary, K. W. and J. M. Nelshoppen. 1991. *Cancer Lett.* 60:169–175). For example, a diet containing 1% of rosemary extract significantly inhibited the initiation of mammary tumorigenesis in rats (Singletary, K. W. and J. M. Nelshoppen. 1991. *Cancer Lett.* 60:169–175). Palpable tumor incidence in rats fed the rosemary extract was 47% less than that of rats fed a control diet. Therefore, rosemary extracts were cancer preventive.

Black tea and its extracts also have been well-studied as potential pharmacological agents. Epidemiological studies have suggested that tea consumption has a protective effect against certain forms of human cancer (Stoner, G. D. and H. Mukhtar. 1995. *J. Cell Biochem. Suppl.* 22:169–180; Fujiki et al. 1996. *Nutr. Rev.* 54:S67–S70). In addition, extracts of black tea in particular have been shown to be potent inhibitors of tumorigenesis in several animal model systems (Javed et al. *Biomed. Environ. Sci.* 11:307–313; Yang et al. 1997. *Carcinogenesis* 18:2361–2365; Weisberger et al. 1998. *Carcinogenesis* 19:229–232; Rogers et al. 1998. *Carcinogenesis* 19:1269–1273). Therefore, black tea extracts are known to be tumor preventive agents.

One of skill would use the knowledge of the biological activity of these other phytochemicals to develop a combination diet or dietary supplement for use to treat or prevent cancer in animals, including humans. Resveratrol analogs may be used in combinations singly or multiply with resveratrol, Mexican Bamboo extract, Huzhang extract, rosemary extract, and black tea extracts. Doses of each compound or extract used in the combination product would be chosen based on known activity of the compound or extract in animals or cells. It is routine for one of skill to extrapolate doses for use in vivo in humans based on studies in cells or animals. For example, human test doses can be extrapolated from effective doses in cell studies, such as $IC_{50}$ values, or from effective doses in vivo by extrapolating on a body weight or surface area basis. Again, one of skill in the art would know how to formulate the combined extracts based on the chemical nature of the extract and the desired effect.

The following non-limiting examples are provided to further illustrate the present invention.

EXAMPLES

Example 1

Isolation and Purification of Analogs from Plant Material

Roots of a plant are repeatedly extracted with 75% methanol (10×4 L) at 45° C. The ethanol extract is filtered and concentrated under vacuum using rotary evaporation (Rotavapor R-110, Buchi, Switzerland) to obtain a solid material. The concentrated material can then be either partitioned with acidified ethyl acetate (3% hydrochloric acid) or pretreated with Amberlite resin and then loaded onto a polyamide column (10.16×124.46 cm), and gradient-eluted with methanol. Extract fractions are collected and identified by comparison with known analog structures.

Example 2

Treatment with Resveratrol Analogs

Azoxymethane (AOM)-induced colon tumorigenesis was produced according to the procedure of Deschner et al. (1992. *Carcinogenesis* 12:1193–1196) with slight modification. Female CF-1 mice (6–7 weeks of age) were given subcutaneous injections of AOM (10 mg/kg) in 100 μl normal saline once a week for 6 weeks. In the first experiment, the mice in group 1 and 2 were given AIN 76A diet and the mice in group 3 were given 2% rosemary extract in AIN 76A diet beginning at 2 weeks before the first dose of AOM. In experiment 2, the mice in groups 1 and 2 were given AIN 76A diet for the entire experiment period, the mice in group 3 were given 0.5% rosemary in AIN 76A diet and in group 4 were given 2% rosemary in AIN 76A diet beginning at 2 week before the firs dose of AOM, during, and continuing until 1 week after the last dose of AOM. The mice in group 5 were given 0.5% rosemary in AIN 76A diet and in group 6 were given 2% rosemary in AIN 76A diet beginning at 1 week after the last dose of AOM and continued until the end of the experiment. The mice were killed at 27 weeks after the last dose of AOM. Similar dosing regimens can be used for other types of extracts and in other models of tumorigenesis in animals.

What is claimed is:

1. A composition comprising an analog of resveratrol, wherein the analog in 3, 4, 4', 5-tetrahydroxystilbene (R-3).

* * * * *